(12) United States Patent
Wright et al.

(10) Patent No.: US 8,517,975 B2
(45) Date of Patent: Aug. 27, 2013

(54) DEVICE AND METHOD FOR PRODUCING THERAPEUTIC FOAM

(75) Inventors: David Dakin Iorwerth Wright, London (GB); Anthony David Harman, London (GB); Garry Hodges, Herts (GB); David John Targell, Scotland (GB); Mark Simpson Yeoman, East Sussex (GB); Jeremy Francis Donnan, Edinburgh (GB)

(73) Assignee: BTG International Ltd. (GB)

( * ) Notice: Subject to any disclaimer, the term of this patent is extended or adjusted under 35 U.S.C. 154(b) by 0 days.

(21) Appl. No.: 13/544,984

(22) Filed: Jul. 9, 2012

(65) Prior Publication Data

US 2012/0273977 A1    Nov. 1, 2012

Related U.S. Application Data

(62) Division of application No. 12/518,479, filed as application No. PCT/GB2007/004943 on Dec. 21, 2007, now Pat. No. 8,235,935.

(30) Foreign Application Priority Data

Dec. 21, 2006  (EP) .................................... 06026562
Dec. 21, 2006  (GB) .................................... 0625649.9

(51) Int. Cl.
*A61M 37/00*      (2006.01)
*A61K 31/08*      (2006.01)
*B01F 3/04*       (2006.01)
*B01F 5/10*       (2006.01)

(52) U.S. Cl.
USPC .................. 604/24; 514/723; 261/29; 261/74

(58) Field of Classification Search
USPC .................. 604/24; 239/337, 343; 514/945; 261/74, DIG. 26
See application file for complete search history.

(56) References Cited

U.S. PATENT DOCUMENTS

| | | | | |
|---|---|---|---|---|
| 4,498,318 A | * | 2/1985 | Mitter | 68/200 |
| 4,657,540 A | * | 4/1987 | Iwamoto et al. | 604/408 |
| 5,066,428 A | * | 11/1991 | Manlowe et al. | 261/29 |
| 5,676,962 A | * | 10/1997 | Cabrera Garrido et al. | 424/423 |
| 7,025,290 B2 | * | 4/2006 | Osman et al. | 239/337 |
| 2007/0112308 A1 | * | 5/2007 | Kay et al. | 604/187 |

FOREIGN PATENT DOCUMENTS

| | | |
|---|---|---|
| EP | 0 091 312 | 10/1983 |
| EP | 0 656 203 | 5/1999 |
| EP | 1 266 682 | 1/2004 |
| EP | 1 180 015 | 12/2005 |
| EP | 1 647 255 | 4/2006 |
| GB | 1 589 306 | 5/1981 |

(Continued)

Primary Examiner — Quynh-Nhu H Vu
(74) Attorney, Agent, or Firm — Finnegan, Henderson, Farabow, Garrett & Dunner, L.L.P.

(57) ABSTRACT

A device and a method for generating therapeutic foam from a sclerosing solution such as polidocanol and a gas which is absorbable or dissolvable in the body comprises a disposable cassette including a liquid container and a flexible chamber containing gas, chamber being formed as a loop. Located in the loop chamber is a foam generating mesh. In use, liquid is introduced into the chamber and then the cassette is inserted into a pumping machine where it is engaged by a peristaltic pump which circulates the contents of the loop chamber through the mesh, thus creating foam. When a steady state is reached, foam may be withdrawn using a syringe via either a port or septum.

14 Claims, 8 Drawing Sheets (56) References Cited

FOREIGN PATENT DOCUMENTS

| WO | WO 02/30237 A1 | 4/2002 |
| WO | WO 2004/062461 | 7/2004 |
| WO | PCT/GB2004/004848 | 6/2005 |
| WO | WO 2006/046202 A1 | 5/2006 |
| WO | PCT/GB2006/001749 | 11/2006 |
| WO | PCT/GB2006/001754 | 11/2006 |
| WO | WO 2006/120461 | 11/2006 |

* cited by examiner

DEVICE AND METHOD FOR PRODUCING THERAPEUTIC FOAM

This application is a divisional of application Ser. No. 12/518,479, filed Jun. 10, 2009, now U.S. Pat. No. 8,235,935, which is a U.S. National Phase of PCT/GB2007/004943, filed 21 Dec. 2007, and claims priority to European Patent Application Number 06026562.6, filed 21 Dec. 2006 and British Patent Application No. 0625649.9, filed 21 Dec. 2006, all of which are incorporated herein by reference.

Sclerosis of varicose veins is based on the injection into the veins of liquid sclerosant substances which, by inter alia causing a localised inflammatory reaction, favour the elimination of these abnormal veins. Until recently, sclerotherapy was a technique selected in cases of small and medium calibre varicose veins, those with diameters equal to or greater than 7 mm being treated by surgery.

An injectable microfoam suitable for therapeutic use, on larger veins in particular, has now been developed and is described in EP-A-0656203 and U.S. Pat. No. 5,676,962 (Cabrera & Cabrera), incorporated herein by reference.

It is known to generate a foam of sclerosing solution and air by drawing up appropriate volumes of air and solution in respective syringes, connecting the syringes by way of a simple connector or three way tap, and then depressing each syringe plunger in turn so as to move the contents back and forth between the two syringes. In this way a reasonably uniform foam may be produced. However, this method suffers from a number of disadvantages.

The physical characteristics and composition of the foam are important both for efficacy and safety, and in the two syringe technique the exact composition and characteristics of the foam will depend on the accuracy with which the gas and liquid components are drawn up and the number of and speed of the plunger movements. In addition there may be difficulties ensuring the sterility of the product. The technique is also rather inconvenient, especially when it is required to make up further foam during the course of a treatment; foam can degrade in a couple of minutes and it is therefore not desirable to make up a large batch and leave it in a container to be drawn up as required.

The inventors of the present application have established that the injection of a foam with air, especially in substantial quantities e.g. over 5 or 10 ml, can have safety implications. In fact, even very small quantities of nitrogen (the major component of air) can have adverse safety implications. These are described in EP-A-1180015 and PCT/GB04/004848, the contents of which is incorporated herein by reference. For this reason, it is desirable that the foam is made with a gas which is substantially completely dissolvable in or absorbable by the body, e.g. in blood. It will be understood that, even if such gas is drawn up into a syringe in the two syringe method described above, there is the potential for air to be incorporated into the foam product inadvertently.

A pressurised canister device for producing sclerosing foam is currently in development and is the subject of a number of patent and applications including EP-B-1180015, the contents of which are incorporated herein by reference. This product is capable of producing a foam which is highly consistent, sterile and made with a gas mixture containing a very low percentage of nitrogen gas, with the foam being delivered conveniently into a syringe immediately prior to use. The foam produced by the canister product has been used in extensive clinical trials and has been demonstrated to be effective in the treatment of varicose veins.

in parallel with the continued development of the canister product, the inventors are developing an alternative foam generating system and method which is capable of producing substantially the same foam as the canister, whilst offering some advantages over the canister. This alternative system and method are the subject of the present application.

Although the requirements for a sclerosing foam for use in sclerotherapy of varicose veins are quite specific, a further advantage of the present invention is that it may be used to make a variety of foams for different applications e.g. in therapy or diagnostics. For example, the bubble size distribution and the density of the foam may be adjusted by using different liquids to make the foam and by altering the ratio of gas to liquid. The foam is continuously renewed as it circulates, and so the specification of the available foam can be tightly controlled, yet the foam is "on tap" and easy to access e.g. during a medical procedure. The gas component of the foam can, of course also be varied at will.

A system is disclosed in WO-2006/046202A1 which has some similarities with the present invention, but is designed for producing a high-density suspension of bubbles in liquid (not a foam) for use as an ultrasound contrast agent. In this system, gas is injected through small apertures into a liquid stream circulating around a loop which may expand its volume by up to 3% to accommodate the gas bubbles.

A system is described in WO-2002/30237A1 which comprises a flexible pouch with a sponge inside it. By manually squeezing the pouch and sponge, liquid and gas within the pouch are foamed. The liquid and gas are not circulated, and it would be difficult if not impossible to create a circulating flow in this device.

In this specification, terms are defined as follows:

"Substantially ambient pressure" means 1 bar plus or minus 25%.

"Substantially without change in pressure" means change in pressure of 25% or less.

"Substantially horizontal" means horizontal plus or minus 30 degrees, in the context of the normal orientation of the device in use.

"Physiologically acceptable blood dispersible gas" means gas which may be substantially completely (i.e. more than 95%, preferably more than 99%) dissolved in or in other ways absorbed by the blood in a short period, i.e. less than 12 hours, preferably less than 1 hour.

According to the invention a device and method for producing therpeutic foam are provided having the features set out in the accompanying claims.

One of the advantages of this system is that it can provide a source of foam which is being conditioned continuously and thus maintained with defined properties for a period of time, so that the clinician can repeatedly withdraw foam as needed, e.g. using a syringe. The system requires a machine, which would normally be installed in the clinic, into which cassettes would be inserted. The machine would obviously have a cost in terms of initial installation and subsequent maintenance. However, the cassettes are likely to be relatively inexpensive to produce.

The device can take a number of forms, a preferred one of which is a cassette which may be disposable. The chamber in which the liquid and gas circulate may have the facility of varying its volume to allow foam to be removed, and this may be provided by some mechanical arrangement such as telescoping or hinged chamber walls. It is preferred, however, that the chamber walls be formed at least partly from a flexible or compressible material, e.g. an aluminium .and plastics laminate material or polypropylene or silicone tubing.

The cassette may essentially consist of a chamber or pathway made of such material, or a combination of different materials including such material, filled with gas and liquid for foaming and adapted to be engaged by a pump e.g. a peristaltic pump to circulate the gas a liquid through a foam generating structure within the chamber or pathway. Alternatively, the chamber may be supplied with only gas or only liquid inside it, the liquid or gas respectively being introduced into the chamber or pathway through an appropriate port or septum prior to generation of foam. In this case, the cassette comprises a housing in which the chamber or pathway is located as well as a container for separately storing the gas or liquid and which is adapted for introduction of the gas or liquid into the chamber or pathway prior to the contents of the chamber or pathway being foamed.

The container may take the form of a carpoule, which is a known device comprising a vial, e.g. a glass vial, with a seal at one end provided by a movable disc or plunger which seals with the internal wall of the vial. At the opposite end of the vial is a port or septum through which the contents may be dispensed by applying pressure to the plunger disc.

An alternative to the carpoule would be a flexible container which is engaged by a roller or some other means to progressively compress it in order to deliver the contents via a septum or port into the chamber.

Whatever form the container takes, it is desirable for the cassette to include a channel of some sort by which the contents of the container may be introduced into the chamber or pathway prior to generation of foam in the chamber. For example, the chamber may communicate with a sheathed hollow needle, i.e. a hollow needle encased in a flexible (e.g. silicone rubber) sheath, which is able to penetrate a septum on a carpoule whilst at all times preserving a seal against ingress of atmospheric gases. The carpoule may be arranged to be slidable in the cassette so that its septum may be pushed against the sheathed needle such that the needle penetrates the sheath and septum to open a flow path between the chamber and carpoule prior to moving the plunger disc in order to dispense the carpoule contents into the chamber.

The chamber may have a part of its wall adapted for engagement by an external pump e.g. a peristaltic pump. This may be a part of an aluminium/plastics laminate wall which has resilient properties imparted to it by some means, e.g. by bonding a resilient material to it (e.g. material similar to that used in silicone rubber or polypropylene or P.V.C. tubing) or placing a resilient structure in side it (e.g. a springy/resilient frame or porous structure such as a sponge). Alternatively, the adapted part of the chamber wall may comprise a piece of resilient tubing e.g. of polypropylene or silicone or P.V.C. bonded to the aluminium/plastics laminate or to an intermediate joint element of e.g. rigid plastics material. The cassette may have an aperture through which the part of the chamber wall may be accessed/engaged by an external pump, e.g. a peristaltic pump.

One of the reasons for using aluminium/plastics laminate for the chamber wall is the ability of this material to provide a barrier to ingress of atmospheric gas, especially nitrogen. It is preferred that the chamber is contains a gas mixture comprising a very low percentage of nitrogen, e.g. less than 0.8%, for reasons discussed above. It is desirable for the cassette to have a shelf life of two years or more; since the cassette would normally be stored in an atmosphere with high nitrogen content (namely air), keeping the nitrogen content of the chamber to acceptable levels involves considerable challenge. It is desirable that not only is the chamber wall made at least in part from this laminate material, but also that the entire cassette is supplied wrapped in a similar laminate material, inside which is a low nitrogen atmosphere, e.g. an atmosphere with the same composition as that inside the chamber. It is also desirable that the interior of the cassette housing be filled with the same gas mixture as the chamber.

If resilient tubing is used for the part of the chamber wall to be engaged by a pump, this can potentially compromise the gas mixture inside the chamber, since such tubing generally will allow nitrogen to enter the chamber at a rate which can compromise the chamber contents within a short time after opening the laminate over-wrap. One way of addressing this problem is to provide a further seal covering the aperture in the housing through which the pump engages the tubing, which would be peeled off immediately prior to use.

In order to achieve the low nitrogen atmosphere not only in the chamber but also inside the cassette housing and also inside the over-wrap, it is desirable to manufacture the cassette in a low nitrogen atmosphere, e.g. an atmosphere of under 0.8% nitrogen, preferably under 0.5% nitrogen, rather than simply filling the chamber, cassette and over-wrap bag with the appropriate gas mix.

It is desirable that the chamber, if appropriate after introduction of gas or liquid, is filled only with the gas and liquid which it is desired to make into foam. It is desirable that all the gas and liquid mixture is turned into foam, for a number of reasons. Firstly, the foam is desirably of predetermined characteristics, which may include density and bubble size range. If all the gas and liquid in the chamber are made into foam, then the starting ratio if liquid to gas will define the density of the foam. Furthermore, if all the gas and liquid are combined into substantially homogeneous foam, it will remove the possibility that sub-standard foam or even pure gas or liquid are withdrawn from the chamber for use.

The geometry of the chamber can affect whether all the gas and liquid are converted into foam: it is desirable that there are no steps or other rapid changes in cross section in the chamber which may cause pooling of liquid or trapping of gas. If there have to be changes in cross section which are relatively sudden, then it is desirable that they be upstream of the foam generating structure. It is desirable that foam of the same characteristics can be maintained by continuing to circulate it in the chamber after an initial quantity has been withdrawn for use. For this to happen, the volume of the chamber desirably adjusts itself automatically when foam is withdrawn, preferably in a non-elastic manner; in other words the chamber wall is not deformed in an elastic manner when the volume is reduced. The chamber is preferably capable of adjusting its volume without any substantial accompanying change in pressure. Desirably, when foam is withdrawn, the chamber wall deforms in a direction transverse to the direction of flow of the chamber contents. Furthermore, desirably the chamber geometry remains substantially free of steps or other rapid changes in cross section after withdrawal of part of the contents.

Preferably, the foregoing applies to withdrawal of up to 20%, preferably up to 50%, more preferably up to 90% or more of the contents of the chamber from its initial filled state. This amounts to a reduction in the volume of the chamber from its initial filled state of up to 20%, preferably up to 50%, more preferably up to 90% or more. The initial filled state does not mean the state where it is not possible for more gas and liquid to be introduced into the chamber without increasing the pressure, but simply means the state at the start of the foam generation operation when predetermined desired volumes of gas and liquid are in the chamber.

The chamber or pathway preferably forms a loop, such that the geometry of the chamber or pathway defines the flow path for the gas and liquid, in use. It is desirable for the part of the chamber which is engaged by an external pump to have a relatively small cross section, yet it is also desirable for the overall dimensions of the chamber to be not unduly large. Therefore, it is desired that the cross section of the chamber vary around the loop or circuit. Desirably, a portion of the chamber defining a major part (i.e. more than 50%) of the internal chamber volume is shaped generally in the form of an "L" or a "U", in either case having a central portion of relatively large cross sectional area and tapering end portions terminating in portions of relatively small cross sectional area.

The pressure in the chamber is preferably substantially at ambient pressure when the chamber is in the initial filled state.

It has been found that if the liquid and gas are circulated in a vertical plane, there is a tendency for liquid to pool at the bottom of the circuit path sometimes. For this reason it is desired that the liquid and gas be circulated in a substantially horizontal plane. For example, the cassette may be adapted to fit onto an external pump unit in an orientation such that the liquid and gas are circulated in a substantially horizontal plane.

In order to minimise pooling of liquid, it is desirable that the foam generating structure or device extend across 50% or more (preferably 70% or more, more preferably 90% or more, still more preferably 100%) of the cross sectional area of the chamber where the structure or device is located. Preferably, the device or structure is mounted in the chamber such that all the circulating flow must pass through the structure or device. If the structure or device does not occupy 100% of the cross sectional area where the structure or device is located, then preferably, a blocking member, device or material or baffle is provided to prevent circulating flow bypassing the foam generating device or structure.

The circulating flow of both gas and liquid desirably passes through the foam generating device or structure to form foam. This is distinct from a flow of gas entering a body of liquid or a flow of liquid entering a body of gas to form foam, though this process may happen in a device according to the invention in addition to the combined circulation of gas and liquid through the foam generating device or structure.

The cassette is preferably disposable and the external pump unit and cassette between them preferably incorporate a feature or features which render the cassette incapable of re-use or at least severely hamper re-use of the cassette. For example, the pump unit may incorporate a blade which is deployed into the cassette after a set period of time in order to disable it. Alternatively the cassette may include some form of unique signature, e.g. an RFID tag or bar code, which is read by the pump unit; the pump unit may then be programmed to function with any individual cassette fitted for a set time only and not to function at all if the same cassette is removed and re-fitted. These features may assist in ensuring sterility of the final product.

The gas mixture in the cassette preferably comprises between 0.0001 and 10% nitrogen gas, preferably between 0.001 and 2% nitrogen gas, more preferably between 0.01 and 1% nitrogen gas, still more preferably between 0.1 and 0.8% or between 0.1 and 0.5% nitrogen gas. The gas mixture preferably comprises at least 10% carbon dioxide, preferably at least 25% carbon dioxide or at least 50%.carbon dioxide or at least 99% carbon dioxide. The mixture preferably comprises at least 50% oxygen gas, and may comprise at least 99% oxygen gas. The gas mixture may comprise 5% or more xenon gas, e.g. 50% or more xenon gas. Gas mixtures which are appropriate for foam sclerotherapy are discussed in patent and patent application numbers EP-A-1180015, WO 04/062461, PCT/GB2006/001754, PCT/GB2006/001749 and PCT/GB2004/004848, the disclosures of which are incorporated herein by reference.

The foam produced by the device at steady state preferably has bubbles in a predetermined size range. Preferably at least 50% by number of the gas bubbles of 25 μm diameter and above are of no more than 200 μm diameter and at least 95% of these gas bubbles are no more than 280 μm diameter.

Bubble sizes are calculated by taking up foam into a syringe through its luer opening, optionally attaching a 21G needle, and injecting foam between two glass slides that are separated using 23.25 micron diameter beads (eg. available as microspheres from Park Labs USA). Maxtascan/Global Lab Image technique was used to analyse bubble size. Diameters of uncompressed bubbles (Dr) were calculated from diameters of bubbles between slides (Df) using the equation $Dr=3\sqrt{3}Df^2x/2$ where x is the distance between the slides. These measurements thus are made at ambient temperature and pressure.

The foam preferably has a density of between 0.7 and 2.5 g/ml, preferably 0.9 to 0.19 g/ml, more preferably 1.1 to 1.6 g/ml. The foam preferably has a half life of greater than 60 seconds, preferably 90 seconds, more preferably 120 seconds, e.g. more than 150 or more than 180 seconds. If a gas mixture having a high percentage, e.g. 50% or more, of carbon dioxide is used, it may be desirable to add a viscosity enhancing agent to the sclerosant and gas mix prior to foaming in order to increase the half life. Suitable viscosity enhancing agents include glycerol or polyvinyl pyrrolidone (PVP).

In another aspect of the invention, a foam generating device for generating therapeutic foam may comprise:
  a) a sealed chamber containing foamable liquid and gas and having a predetermined initial volume;
  b) a foam generating structure located within the chamber;
  c) whereby a therapeutic foam may be generated by circulating the gas and liquid through the foam generating structure within the chamber;
  d) the chamber being of variable volume and, on extraction of therapeutic foam from the chamber, being capable of reversibly reducing its volume by 20% or more, preferably 50% or more, from the said predetermined initial volume, without substantial change in pressure, whilst still permitting circulation of gas and liquid to maintain the remaining foam in the chamber.

At its predetermined initial volume the chamber may be at substantially ambient pressure, and ambient pressure in the chamber may be substantially preserved following extraction of foam causing the said volume reduction of 20% or more, preferably 50% or more.

Preferably, at least one part of the wall of the chamber is of flexible or compressible material by means of which all or part of the said 20%, preferably 50%, reduction in volume is realised.

Preferably, the device includes a pump arranged to circulate the gas and liquid through the foam generating structure within the chamber. The pump may be external to the chamber and arranged to engage the flexible or compressible material of the chamber wall in order to circulate the gas and liquid within the chamber. An external pump helps to ensure sterility of the contents of the chamber. The chamber may be provided within a disposable cassette, unit or consumable adapted to be mounted on the external pump such that the gas and liquid circulate within the chamber in a substantially horizontal plane. Horizontal circulation helps to eliminate dead spots in the flow within the chamber. The chamber is preferably formed as an endless loop, thereby defining a continuous pathway around which liquid and gas may circulate.

In another aspect, the invention may comprise a cassette, unit or consumable for use in generating therapeutic foam which comprises a chamber charged with physiologically acceptable, blood dispersible gas with less than 5%, preferably less than 2%, of any other fluid present, the chamber being in the form of an endless loop defining a continuous pathway around which its contents may circulate, a foam generating structure being located in the said pathway. The gas preferably consists essentially of carbon dioxide and/or oxygen gas. The chamber may be capable of increasing its volume by 10% or more, preferably 20% or more, without any substantial change in the pressure in the chamber, to allow introduction of liquid. The chamber wall may be at least partly of flexible or compressible material. The chamber may be located in a housing, in which case the housing preferably has an aperture through which a flexible or compressible part of the wall of the vessel may be engaged by an external pump, in use, in order to circulate The contents of the chamber.

The cassette, unit or consumable may further comprise a sealed container charged with foamable liquid, the said container being arranged for the selective introduction of its contents into the chamber such that the chamber then contains both gas and foamable liquid. The container may also be located in the housing.

In another aspect, the invention may be described as a cassette, unit or consumable for use in generating therapeutic foam which comprises:
  a) a sealed chamber containing gas or foamable liquid, the chamber being in the form of an endless loop defining a continuous pathway around which the liquid and gas may circulate, a foam generating structure being positioned in the pathway such that, in use, flow of the chamber contents around the pathway passes through the said structure;
  b) a sealed container charged with foamable liquid or gas, respectively; the said container being arranged for the selective introduction of its contents into the said chamber.

For example there may be a valve or a septum and hollow needle arrangement whereby liquid or gas may be introduced from the container into the chamber. The container may be initially charged with liquid and the chamber may be initially charged with gas. This is the preferred arrangement.

The sealed chamber is preferably of variable volume, capable of increasing its volume by 10% or more, preferably 20% or more, to allow introduction of gas or liquid without any substantial change in the pressure in the chamber. This increase in volume is defined with respect to the volume of the chamber in a "pre-activated" state in which the chamber contains only gas or only liquid and the container contains only liquid or only gas, respectively. This increase in volume brings the volume of the chamber up to what could be described as a "predetermined initial volume" which is the internal chamber volume at the start of the foam generating operation. Once foam has been generated and it is desired to remove foam for use, the chamber is capable of accommodating this whilst still allowing the remaining foam to be circulated to maintain its properties. In order to do this, the chamber may be capable of reducing its volume by 20% or more, preferably 50% or more, from the "predetermined initial volume" without any substantial change in the pressure in the chamber on extraction of the foam, whilst still permitting circulation of gas and liquid to maintain the foam remaining in the chamber. By "substantial change" is meant a change of more than 25%.

The liquid may be any foaming solution or a mixture of an active agent and a foaming agent, but is preferably a sclerosing solution. For example 1% polidocanol solution is preferred, though concentrations of polidocanol between 0.25 and 5% could also be used, and other sclerosants e.g. sodium tetradecyl sulphate solution e.g. between 1% and 3% could be used. The contents of the chamber are preferably sterile and preferably also pyrogen free.

The chamber is preferably provided with access means, preferably access means for a syringe luer nozzle or needle and taking the form of a septum, sealable port or valve. In this way, foam may be withdrawn conveniently from the device.

The foam generating structure preferably comprises an element defining at least one passage of cross sectional area $1\mu^2$ to 10 $mm^2$, preferably $10\mu^2$ to 5 $mm^2$, more preferably $50\mu^2$ to 2 $mm^2$, through which gas and liquid pass when they are propelled around the loop. The maximum dimension of the passage or passages is preferably between $0.1\mu$ and 2 mm, more preferably between $1\mu$ and 1 mm, more preferably between $2\mu$ and $500\mu$, still more preferably between $3\mu$ an $100\mu$. The passage or passages is/are preferably provided by at least one element comprising one or more meshes, screens or sinters. Two or more elements are preferably provided, at least two of the said elements optionally being spaced apart in the direction of flow by between 0.1 mm and 10 mm, preferably between 0.5 mm and 5 mm.

In preferred embodiments, the liquid container is a carpoule, which is a known device comprising an ampoule or vial, e.g. of glass, with an open end and a closed end which is fitted with a septum cap. The vial is fitted with a sealing plunger head which can slide down the vial to expel the contents of the vial via the septum cap, after the cap has been punctured by a needle.

Further features and advantages of the invention will be apparent from the following description of a number of specific embodiments, which is given by way of example only and with reference to the following drawings.

Referring firstly to FIGS. 1 to 4, a cassette for the production of sclerosing foam suitable for use in the treatment of varicose veins comprises a housing 1 of polypropylene or other suitable plastics material having a flat profile, about 10 cm in length, 7 cm in width and 1 cm in thickness. The top and edge walls are partly cut away on one side of the housing to provide a recess 2, whilst on the opposite side of the housing 1 a standard luer-type port 3 is provided, suitable for receiving a standard luer-type syringe nozzle in a sealing fashion.

Figure 1:
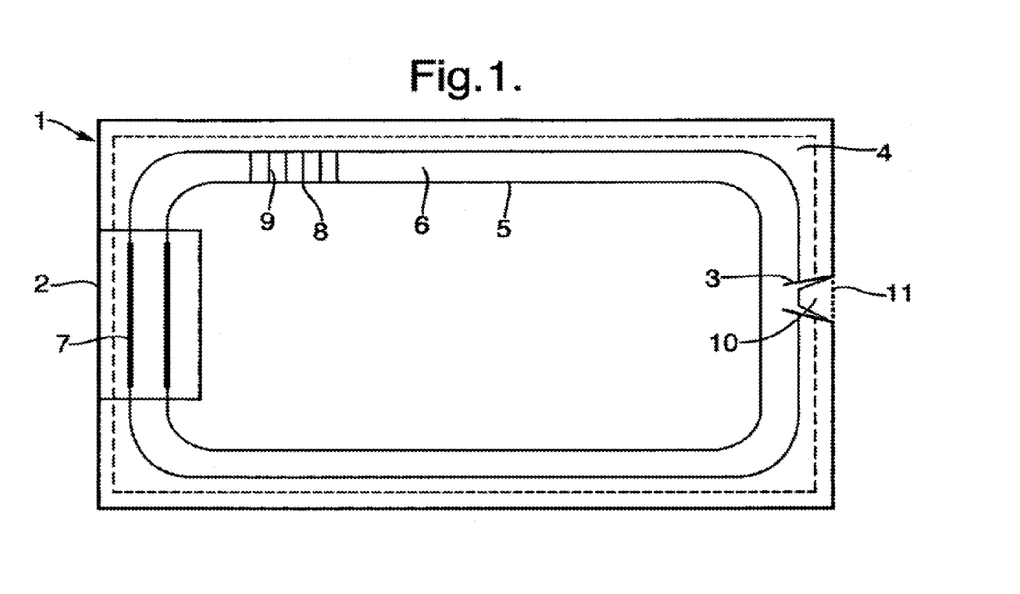
FIG. 1 is a schematic sectional plan view of a first embodiment of cassette in accordance with the invention.

Within the housing 1 is located a pouch 4 of metallised plastic laminate material, e.g. of aluminium and polyethylene, the outer extent of which is shown in FIG. 1 as a dashed line. Such material is well known and is both relatively impervious to gas transfer and also relatively inexpensive. The pouch 4 comprises two sheets of laminate material joined together along seam lines 5, e.g. by ultrasound or heat welding, to define a chamber 6 in the form of an endless loop. Welded into the outer of the two seams 5 is a polypropylene luer port unit 3. Fitted into the port 3 is a complementary stopper 10 which forms a substantially gas-tight seal with the port. The port 3 is further sealed with a gas-impermeable membrane 10 of the same metallised plastics laminate material secured to the outer edge of the port unit 3 with an adhesive of a type which allows the membrane 10 to be peeled off prior to use.

On the opposite side of the cassette, over a portion 7 of the loop, the pouch material is reinforced on each side with an external layer. of relatively thick (approximately 1 mm) resilient material such as PVC or silicone rubber, which has been pre-formed with a semi-circular cross section. The result is that this portion of the loop behaves similarly to a piece of resilient tubing made from the PVC or silicone rubber material. The reinforced portion 7 of the loop coincides with the recess 2 in the housing and is therefore exposed, as can best be seen in FIG. 2. An alternative construction is provided by locating a similar length of resilient (e.g. PVC or silicone) tubing inside the pouch in the same portion of the loop. Another alternative would be to provide the pouch with a cutaway portion approximately corresponding to the shape of the housing in the recess, such that the chamber 6 formed by the pouch is interrupted at the side edges of the cutaway portion, leaving opposed openings in the pouch into which the ends of a section of resilient tubing are bonded to complete the loop chamber 6.

Located within the loop chamber 6 is a foam generating structure 8 formed of a series of mesh elements 9. Each mesh element comprises a flat cylindrical member of plastics material, the internal diameter of which is spanned by a mesh material. Five of these mesh elements are arranged in a stack as shown in FIG. 1. The mesh elements are known in themselves and are described e.g. in EP-A-1266682. This is a similar structure to that used in the canister product referred to above and described in e.g. EP-B-1180015. Alternative foam generating structures may be provided. It is believed that, due to the continuous circulating mode of operation of the device of the present invention, the exact properties of the foam generating element are not critical and that a baffle or series of baffles or a labyrinthine path or even a simple constriction or obstruction may be sufficient to produce a foam of the desired properties.

The loop chamber 6 is charged with 8 ml of sclerosant liquid, e.g. a 1% aqueous solution of polidocanol. Other concentrations of polidocanol are possible, and other sclerosants will be known to those of ordinary skill in this field, e.g. sodium tetradecyl sulfate, ethanolamine oleate, sodium morrhuate, hypertonic glucosated or glucosaline solutions, glycerol, chromated glycerol or iodinated solutions.

The loop chamber 6 is also charged with 50 ml of gas. The gas comprises a mixture of 70% oxygen and 30% carbon dioxide, with less than 0.5% nitrogen gas impurity. Other gas mixtures are possible, but this mixture is preferred for reasons which are set out in published patent applications EP-B-1180015 and PCT/GB04/004848.

The entire cassette is sealed in a gas tight package of metallised plastic laminate material, which also forms a sterile barrier.

To produce foam, the cassette described above is inserted into a pumping machine which propels the liquid and gas around the loop chamber 6 to create foam which may then be tapped off via the luer port 3. A pumping machine is illustrated schematically in FIG. 5. The machine is a desk-top device comprising a main housing 70 in which is formed a slot 71 for receiving a cassette 72 as described above. On the exterior of the casing 70 is a control panel 73 with a "foam ready" indicator light 74, a digital display 75 and an on/off switch 76.

Figure 5:
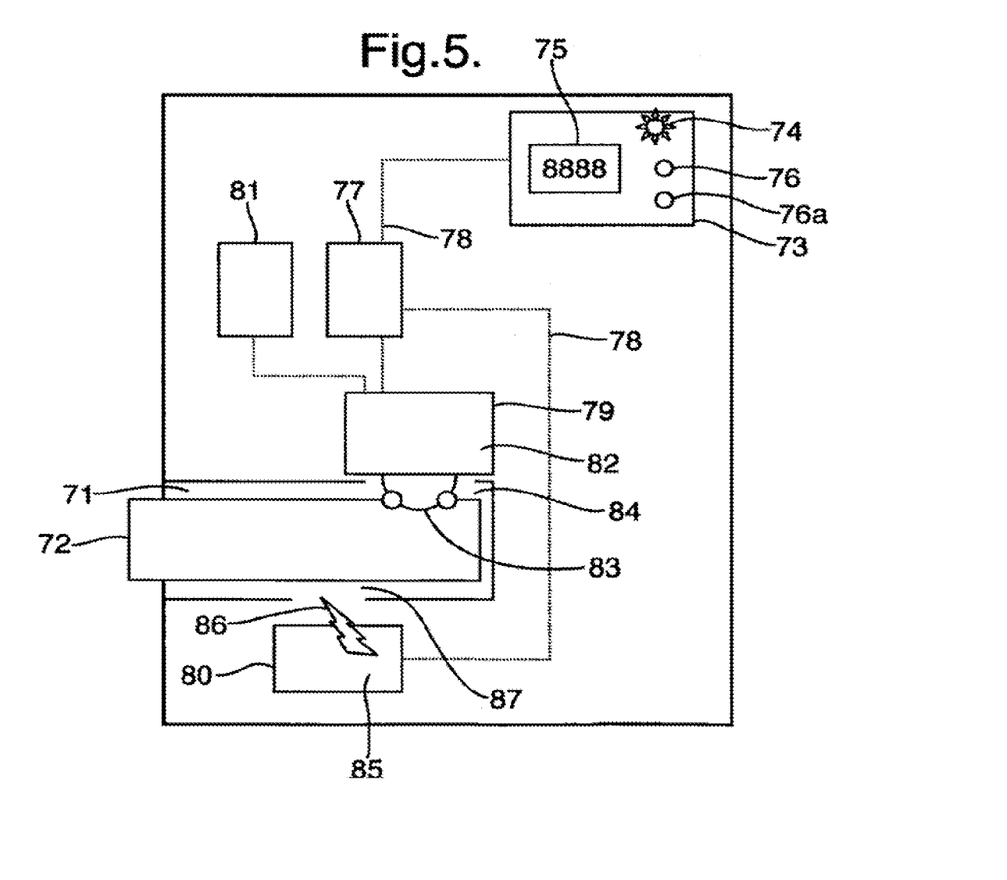
FIG. 5 is a schematic representation of a pumping machine in accordance with the invention.

Inside the casing is a microprocessor controller 77 connected by various signal lines 78 to a pump unit 79, to the control panel 73 and to a cassette disabling device 80.

The pump unit 79 is connected to a power source 31 (which could be a battery or a transformer receiving power from a mains supply—not shown). The unit may be standard peristaltic pump of the type used in many medical applications including e.g. dialysis machines. As schematically illustrated in FIG. 5, the pump comprises a motor 82 driving a roller unit 83 which projects through an aperture 84 in the casing into the cassette slot 71. When a cassette 72 is inserted in the slot 71 (as shown in FIG. 5), the roller engages with the exposed resilient portion 7 of the loop chamber wall (see FIGS. 1 & 2).

The cassette disabling device 80 comprises a solenoid actuator 85 and a blade 86 located adjacent a second aperture 87 in the casing within the slot 71.

Figure 2:
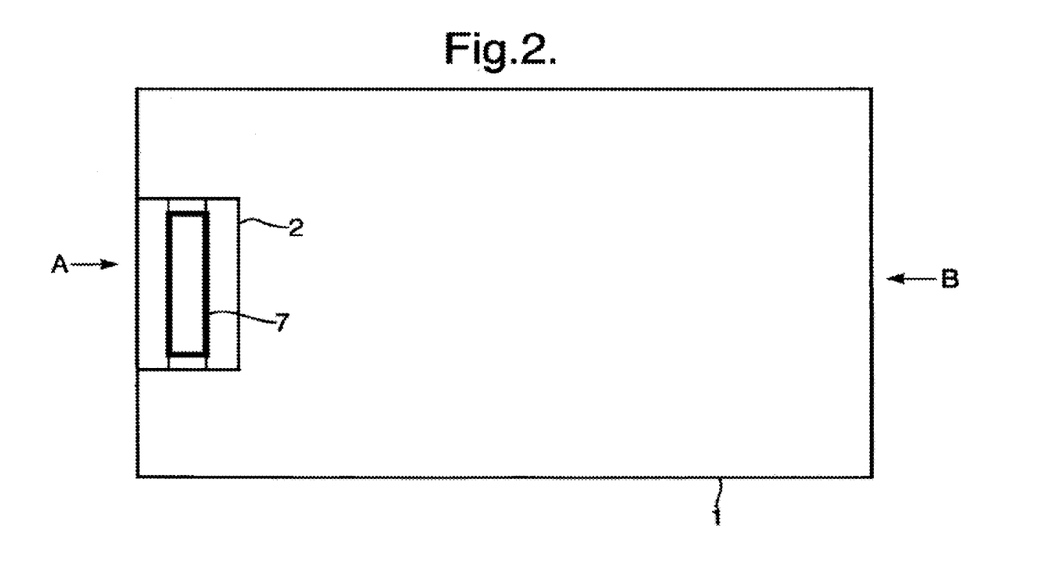
FIG. 2 is a simple schematic plan view of the cassette of FIG. 1.
Figure 3:
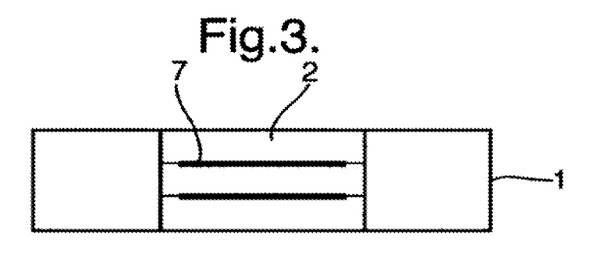
FIG. 3 is a schematic view of the cassette of FIGS. 1 and 2 in the direction A.
Figure 4:
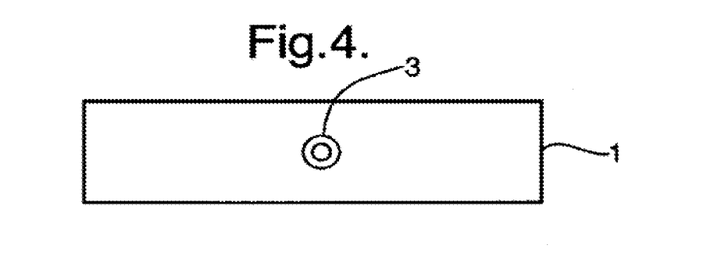
FIG. 4 is a schematic view of the cassette of FIGS. 1, 2 and 3 in the direction B.

In use, a cassette 72 is inserted into the slot 71 in the machine immediately prior to the foam being required for treatment of a patient (or other use), with the sealed luer outlet 3 on the exposed side of the cassette. The machine is then switched on and the pump unit engages with the exposed resilient portion 7 of the loop chamber wall through the recess 2 in the cassette housing 1. The pump then proceeds to move the liquid and gas around the chamber in .a peristaltic movement which is well known and understood in this field. As the fluid is moved around, it passes through and interacts with the foam generating meshes 8 and is mixed and then the mixture subjected to shear forces as it repeatedly passes through the meshes, which. cause it to turn into a fine microfoam. A steady state is reached after about 30 seconds, where the properties of the foam remain essentially constant. Foam of this sort tends to decay relatively fast if left alone; this process is counteracted by the continuing circulation of the foam through the mesh stack 8. A very advantageous feature of this device is that the entire volume of foam is continuously recirculated so that, whilst it is circulating, all of the foam has properties which can be known to a high degree of precision.

The microprocessor control unit 77 causes the "foam ready" indicator light 74 to illuminate after a period sufficient to ensure that the foam has reached steady state, i.e. has substantially constant properties which can be known. This period of time could be e.g. 30 seconds or one minute. At this point, an operator may temporarily stop the machine using the "pause" button 76a, peel off the membrane seal 11 from the luer outlet 3, then remove the stopper 10 and insert a syringe having a standard luer nozzle and withdraw foam for use. Normally, about 15 ml of foam might be withdrawn. This represents only some of the foam in the cassette, which contains about 60 ml. The stopper 10 may then be reinserted and the machine reactivated by pressing the "pause" button 76a again, to maintain the remaining foam in condition until a further aliquot is required. In a modification of the first embodiment, the controller 77 is programmed to re-start the machine automatically when a given time has elapsed after pressing the "pause" button 76a, e.g. 1 minute. Optionally, an audible alarm may sound 5 seconds before the machine restarts.

In order to avoid prolonged use which may lead to compromised sterility and gas composition, the controller 77 is programmed to stop the machine after 30 minutes. Remaining time is displayed on the display 75. Optionally, an audible alarm sounds 5 minutes before the machine stops. At the end of the operational period, the pump stops and the controller 77 causes the solenoid actuator 85 of the cassette disabling device 80 to drive the blade 86 through the aperture 87 and into the cassette. The controller then causes the solenoid actuator to retract the blade to allow the cassette to be removed. The cassette is thereby damaged and its further use is prevented. This is a safety feature which is intended to prevent reinsertion of a cassette which has been used but still has fluid left in it. Reuse of a cassette may compromise sterility, and in any event there is only a limited time for which the gas constituents remain in specification once the outer packaging is removed.

In a modification of the first embodiment, the port 3 is provided with a septum in place of the stopper 10 and membrane 11. Access to the chamber 6 is then possible using a syringe fitted with a needle. The septum preferably has sufficient thickness (e.g. 3 mm or more) that the insertion of the bevelled end of a needle will not cause leakage of gas into or out of the chamber 6 to the surroundings. In this event, there is of course no need for the port unit 3 to have a luer configuration. In another modification, the septum could be provided as a reinforced, resilient portion of the loop, with a similar construction to the portion 7. In a further modification, the luer port and peelable seal membrane are retained but a valve is provided in place of the stopper 10. The valve is arranged to open on insertion of the luer nozzle of a syringe, but otherwise to remain closed to prevent the transfer of gas or liquid between the chamber 6 and the surroundings. All of these modifications of the first embodiment have the advantage that the pump need not be stopped when a syringe nozzle or needle is inserted to withdraw foam. In these modifications, the pause button 76a may be omitted.

Figure 6:
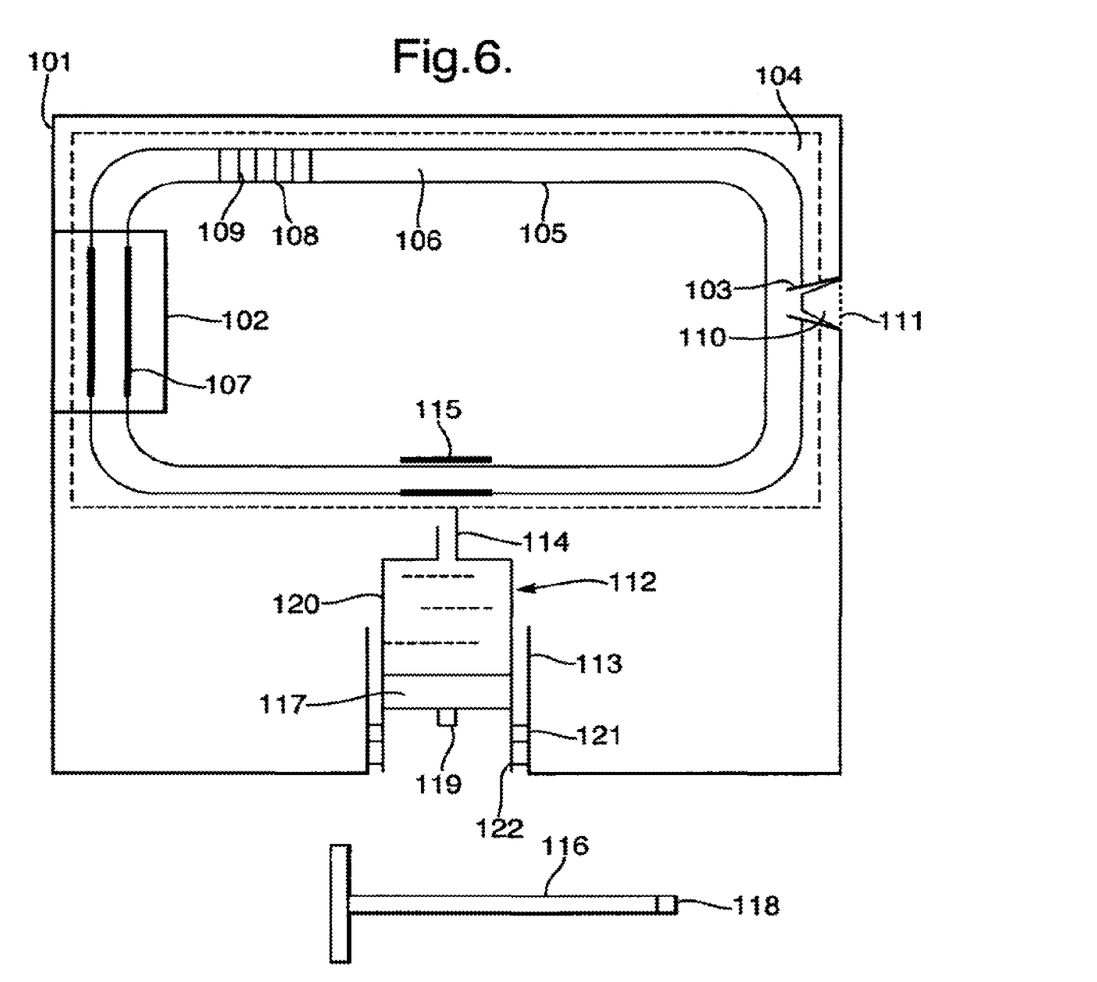
FIG. 6 is a schematic sectional plan view of a second embodiment of cassette in accordance with the invention.

A second embodiment is shown in FIG. 6. In most ways this embodiment is the same as the first and reference numerals correspond, but with the number series for the second embodiment commencing at 101 rather than 1. In the second embodiment the loop chamber 106 contains only gas in the cassette as supplied. The 5 cassette housing 101 is somewhat larger and accommodates a syringe device 112 slidably mounted in a syringe recess 113 the. housing 101. The syringe device comprises a glass container (or cartridge 120 containing 8 ml of 1% polidocanol solution, fitted with a movable sealing plunger element 117 and with a needle 114. Such containers are well known in themselves. The container is mounted in a ring 121 of resilient material which provides a degree of resistance to sliding. A flange 122 is provided at the proximal end of the container. A second resilient portion of the chamber loop wall is provided in the second embodiment, to act as a septum 115. A luer port 103 is provided with a stopper 110 and a membrane 111.

As with the first embodiment, the cassette is packed in a sterile metallised plastic laminate. In the case of the second embodiment, the pack also includes a syringe plunger shaft 116. The plunger shaft 116 is fitted with a snap lock formation 118 arranged to engage a complementary formation 119 on the plunger element in the container 120.

The second embodiment is obviously somewhat more complicated to use than the first. However, the more complex arrangement means that sterilisation of the polidocanol container and of other parts of the cassette may be performed separately, which may be advantageous.

In use, the loop chamber 106 is charged with polidocanol solution from the container 120 prior to inserting the cassette into the pumping machine. The operator fits the plunger shaft 116 onto the plunger element 117 using the co-operating snap lock formations 118 and 119. As the operator applies pressure to the plunger, the cassette moves forward through the resilient ring 121 until the flange 122 at the proximal end of the container engages the ring and prevents further movement. At this position, the needle 114 has pierced the septum 115 and its tip is located within the chamber 6. As continued pressure is applied to the plunger 116, the plunger clement 117 advances within the container to deliver the contents into the loop chamber 6. The resistance to relative movement between the container and ring is arranged to be lower than the resistance to movement of the plunger element 117 within the container 120, so that the needle always penetrates the septum before delivery of the container contents.

Once the polidocanol has been delivered to the loop chamber 6, the plunger 116 is snapped off and the cassette inserted into the pumping machine of FIG. 5. The pumping machine is the same as for the first embodiment of cassette, except that the dimensions of the slot 71 are adjusted to accommodate the larger cassette.

Many modifications and alternatives will be apparent to the skilled reader. For example, it is not essential that the chamber 6 be in the form of a loop. Provided the pump is able to cause a circulating flow within the chamber which interacts with the foam generating structure, the same effect is achieved.

The pump need not necessarily be a peristaltic pump. It is possible that a magnetic pump member could be provided inside the chamber 6, which is driven by an external drive in the pumping machine in a similar way to a conventional laboratory magnetic stirrer. It is possible that the internal pump member could itself generate an adequate foam in which case the "foam generating structure" of such an embodiment could be constituted by the pump member.

In another modification, the flow direction of the pump may be periodically reversed to ensure that there are no "dead spots" in the chamber 6 where the flow is not sufficiently energetic, causing a build-up of foam which does not have the correct properties. In such an embodiment, the flow would still be a continuous, circulating flow, but the direction would be reversed e.g. every 2-10 seconds resulting in the fluid mix/foam passing through the foam generating means in a different direction.

FIGS. 7 to 12 show a third embodiment of the invention. In many ways this embodiment is similar to the second embodiment. Reference numerals correspond for similar parts, but with the number series for the third embodiment commencing at 201 rather than 101.

Figure 7:
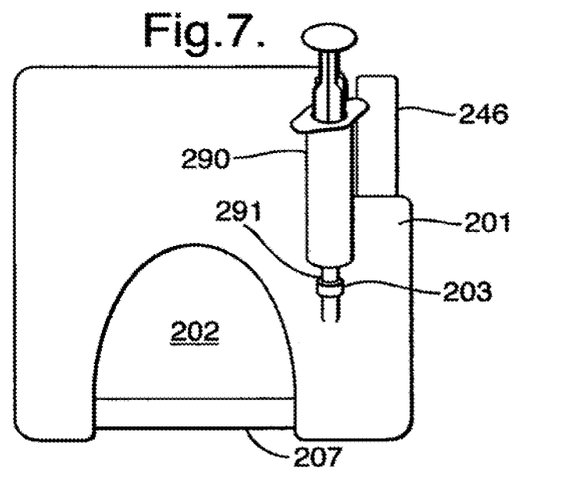
FIG. 7 is a view from above of a third embodiment of cassette in accordance with the invention, with a syringe fitted to its outlet port.

Referring firstly to FIG. 7, the cassette comprises a main housing 201 of ABS (acrylonitrile butadiene styrene). The cassette housing has a cutaway portion or recess 202, extending across which is a section of polypropylene tubing 207, suitable for being engaged by an external peristaltic pump. Projecting from the top face of the cassette at an angle of about 30 degrees is a short outlet tube 231 incorporating a valved luer port 203. In FIG. 7 a conventional plastic syringe 290 is shown with its luer nozzle 291 inserted into the port 203.

Figure 8:
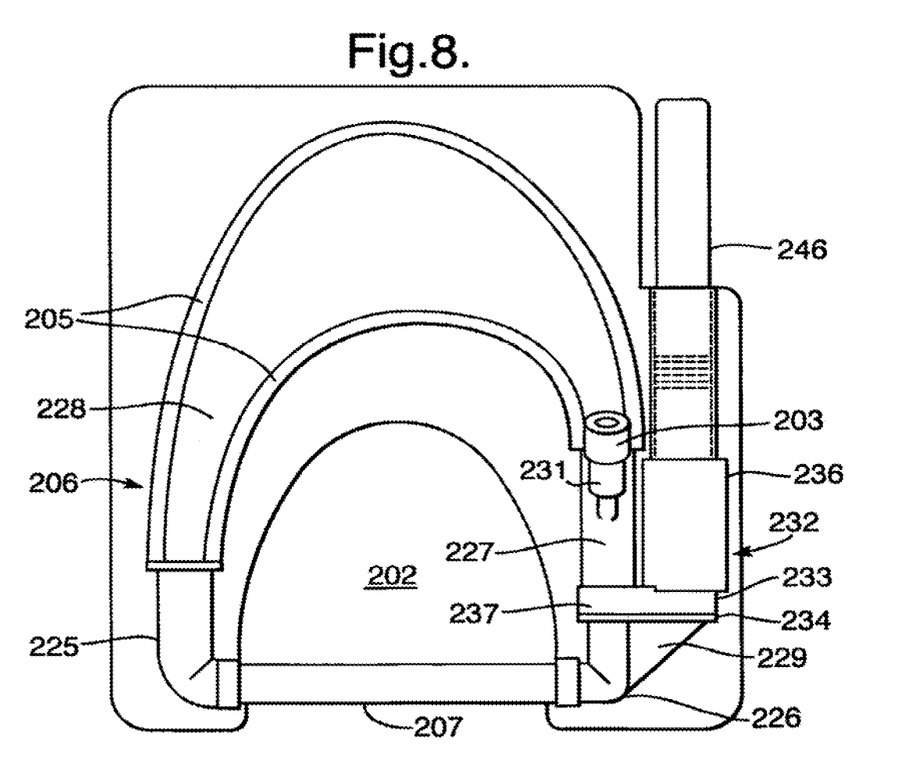
FIG. 8 is a view from above of the embodiment of FIG. 7, with the cassette casing partly cut away.

Turning now to FIG. 8, the cassette is shown with the top half of the housing 201 removed so that the interior can be seen. A loop chamber 206 is made up from a number of parts including a generally U shaped pouch 228 of three-layer aluminium plastic laminate film with heat welded seams 205 and the peristaltic tube 207 referred to above. An L shaped tube 225 of rigid high density polyethylene is secured using adhesive to the pouch 228 at one end and to the peristaltic tube 207 at the other. A second corner tube 226, also of high density polyethylene, is secured using adhesive to the other end of the peristaltic tube 207. The second corner tube incorporates a laterally extending triangular support flange 229 with a face plate 234 along one edge, whose function will be explained below. Secured by adhesive to the face plate 234 of the second corner tube is a joint member 232 of high density polyethylene, comprising a short section 237 which, when the joint member is assembled, is in registry with the bore of the corner tube 226 and also the bore of a straight section 227 of high density polyethylene tube, from which projects the outlet tube 231. The other end of the straight section 227 is secured by adhesive to the other end of the laminate pouch 228, thereby completing the loop 206. The loop is charged with 38 ml of a gas mixture comprising 30% carbon dioxide and 70% oxygen, with under 1% nitrogen contamination.

Returning now to the joint member 232, the short section 237 has a laterally extending flange 233 which abuts the face plate 234 and forms with it a channel 235 (best seen in FIG. 10) leading into the main loop chamber 206. The joint member 232 also comprises a cylindrical carpoule socket 236 which extends in parallel with the straight tube section 227 in the assembled device. The function of this component is described below.

Figure 9:
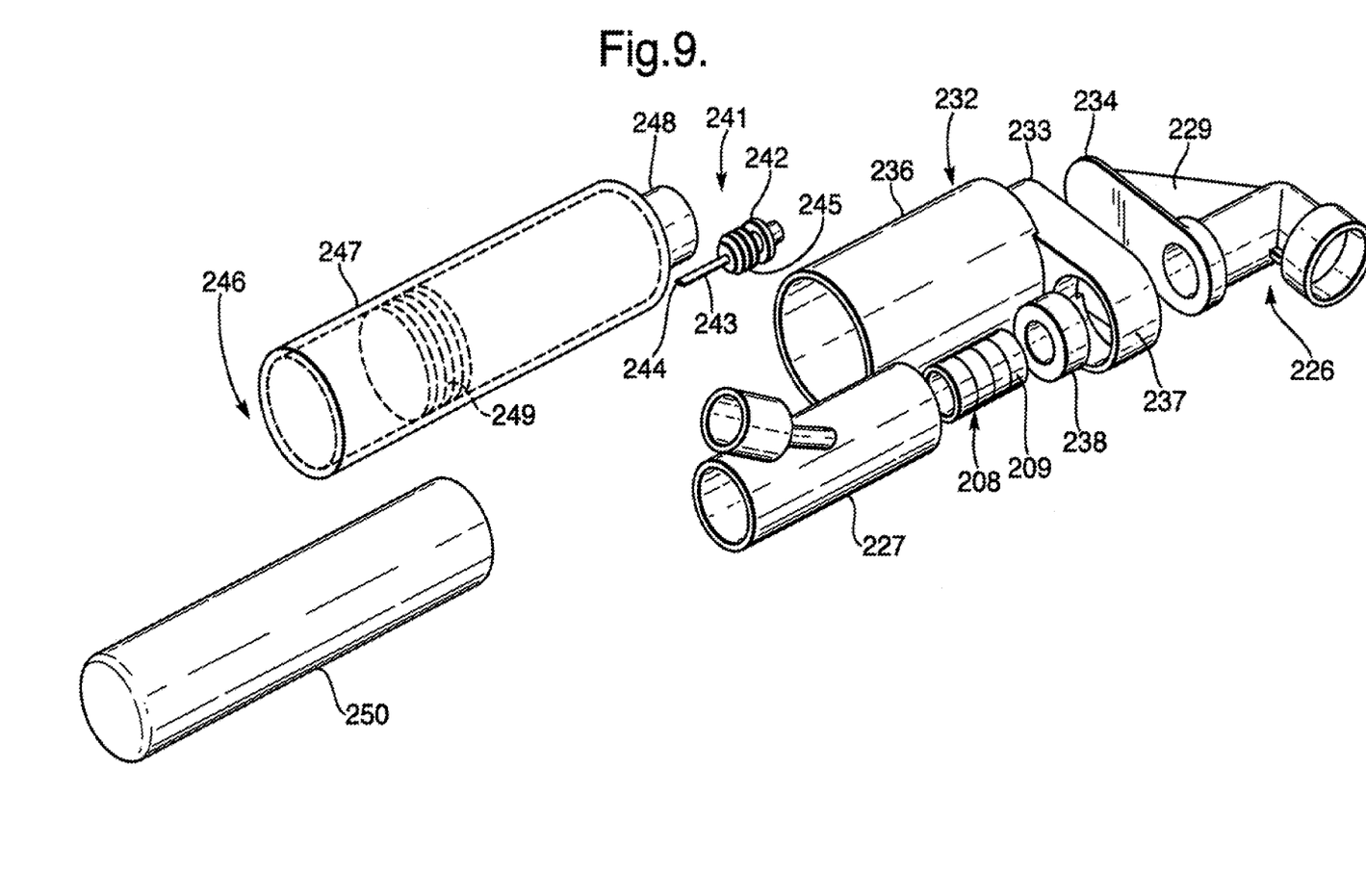
FIG. 9 is an exploded perspective view of part of the embodiment of FIG. 7, showing those parts associated with introduction of liquid into the cassette chamber.

Turning now to FIG. 9, a porous ring component 238 of sintered metal is shown, which in the assembled device would be located within the short channel section 237 of the joint component 232. Next to this is a foam generating structure 208 comprising a stack of mesh elements 209, each of which consists of a ring with a microporous membrane stretched across it. In this example the membrane has pores of maximum dimension 6 micron and has a total open area of about 5%. The mesh stack is located within the straight tube section when the device is assembled.

Figure 11:
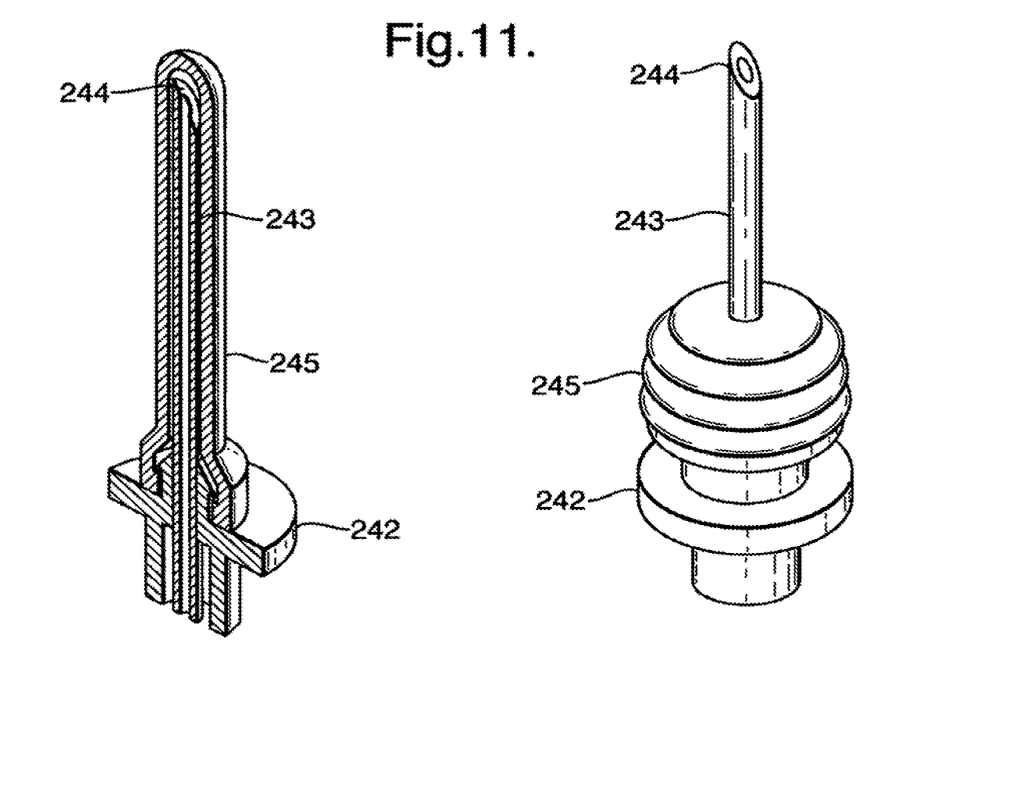
FIG. 11 is a perspective view and a perspective cutaway view of a sheathed needle which forms part of the embodiment of FIG. 7.

The cylindrical carpoule socket 236 referred to above comprises an end plate 239 in which is an orifice which communicates with the channel 235 leading to the main loop chamber 206. On the interior side of the end plate 239, surrounding the orifice is an annular mount 240 in which is received a sheathed needle assembly 241. The needle assembly comprises a base 242 of polyethylene which is received into the orifice and annular mount 240 so as to form a seal between the mount and the base. Moulded into the base 242 is a hollow stainless steel needle 243 which communicates with the channel 235 leading to the chamber 206, and also extends part of the way along the axis of the cylindrical socket 236, such that its pointed end 244 is located part of the way along the socket 236. Attached by adhesive to the base 242 is a sheath 245 of silicone rubber which extends over the length of the needle 243 and encloses it.

Received in the socket 236 is a carpoule 246 of a design which is standard in the pharmaceutical industry, consisting of a glass cylinder or vial 247, open at one end and with a septum seal cap 248 fitted at the other. Within the glass vial is a sealing plunger head 249 of silicone rubber capable of being moved toward the septum cap end of the vial. Also received in the proximal end (vis a vis a user) of the vial and butted against the sealing plunger head 249 is a plunger shaft 250 of ABS.

The carpoule 246 is received in the socket 232 as a gentle interference fit so that it is retained in place in the socket 232 but is also able to be moved along the axis of the socket relatively easily. The carpoule contains 5 ml of 1% polidocanol solution.

The whole cassette, including carpoule, is packaged in 5 layer aluminium plastic laminate membrane. This material has two layers of aluminium, which make it highly resistant to gas transfer. It is important that nitrogen, which constitutes 80% of atmospheric air, does not transfer into the gas chamber in appreciable amounts. The 5 layer laminate packaging ensures that the product can have a shelf life of 2 years with only a fraction of 1% ingress of nitrogen.

The manufacture of the cassette involves the following stages. The various components making up the loop chamber 206 are assembled in at atmosphere either of the 30% CO2, 70% O2 gas mix with which the chamber will be filled, or an atmosphere of >99% pure carbon dioxide, the latter being safer. In either event, the nitrogen content of the atmosphere is kept to a minimum practical level and certainly below 1%. Whilst still in this atmosphere, the loop chamber 206 is assembled to the housing 201 and a gas tight seal of three layer plastics aluminium laminate film is secured over the recess in the housing to provide an additional degree of protection against nitrogen ingress; the reason for this is that the polypropylene peristaltic tube is the most vulnerable part of the assembly for nitrogen ingress. This unit is then autoclaved.

Meanwhile the carpoule 246 is filled with 5 ml of 1% polidocanol and heat sterilised. The carpoule 246 is then assembled to the housing 201 and then, in the same atmosphere, the entire cassette assembly is overwrapped with a 5 layer aluminium plastics laminate film pouch. In this way, it is ensured that the space between the overwrap pouch and the cassette contains little or no nitrogen gas. If the manufacturing process has been carried out in a CO2 atmosphere, then a flushing operation is then required, which involves partly evacuating the chamber and then injecting oxygen gas in sufficient quantity into the port of the chamber so as to bring the contents up to 70% O2. Then a similar process is performed for the internal space in the housing and then for the space in the overwrap bag, which is then sealed.

Figure 12:
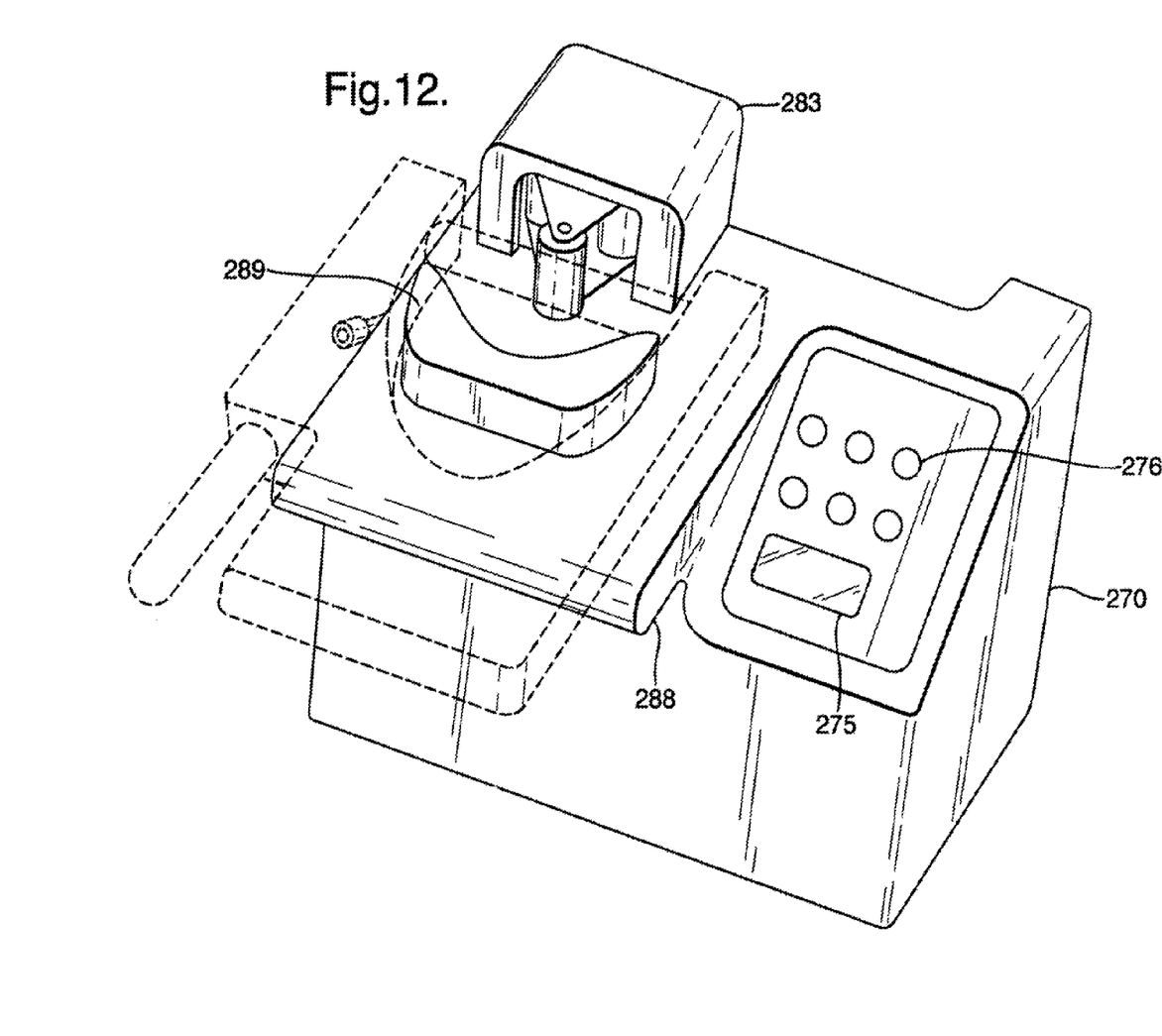
FIG. 12 is a schematic perspective view of a pump unit of the third embodiment of the invention.

FIG. 12 shows a peristaltic pump unit with a cassette as described above and depicted in FIGS. 7 to 11 fitted onto the pump unit, shown in dashed lines. The pump unit is an adapted version of a Watson Marlow Sci Q 323 peristaltic pump and comprises a housing 270 and a control panel including on/off switch 276 and digital display 275. The adaptation of the Watson Marlow unit comprises changes to allow it to be operated in an orientation shifted through 90 degrees from its normal operating position. This allows the cassette to be mounted on the pump in a horizontal orientation as shown: the display and surface indicia have been changed to accommodate this. The pump head 283 and backing plate 289, which is slidably mounted on the pump unit, have been redesigned to accommodate the shape of the cassette and a ledge 288 has been provided to support the cassette when mounted on the pump.

In use, when it is desired to make polidocanol sclerosant foam shortly before treating a patient, a cassette is removed from its wrapping and fitted onto the pump by positioning it with the peristaltic tube 207 between the pump head 283 and the backing plate 289 as shown in FIG. 12. The backing plate 289 is then slid against the peristaltic tube 207, pressing it against the rollers of the pump head 283, until the slidable backing plate locks into position.

Figure 10:
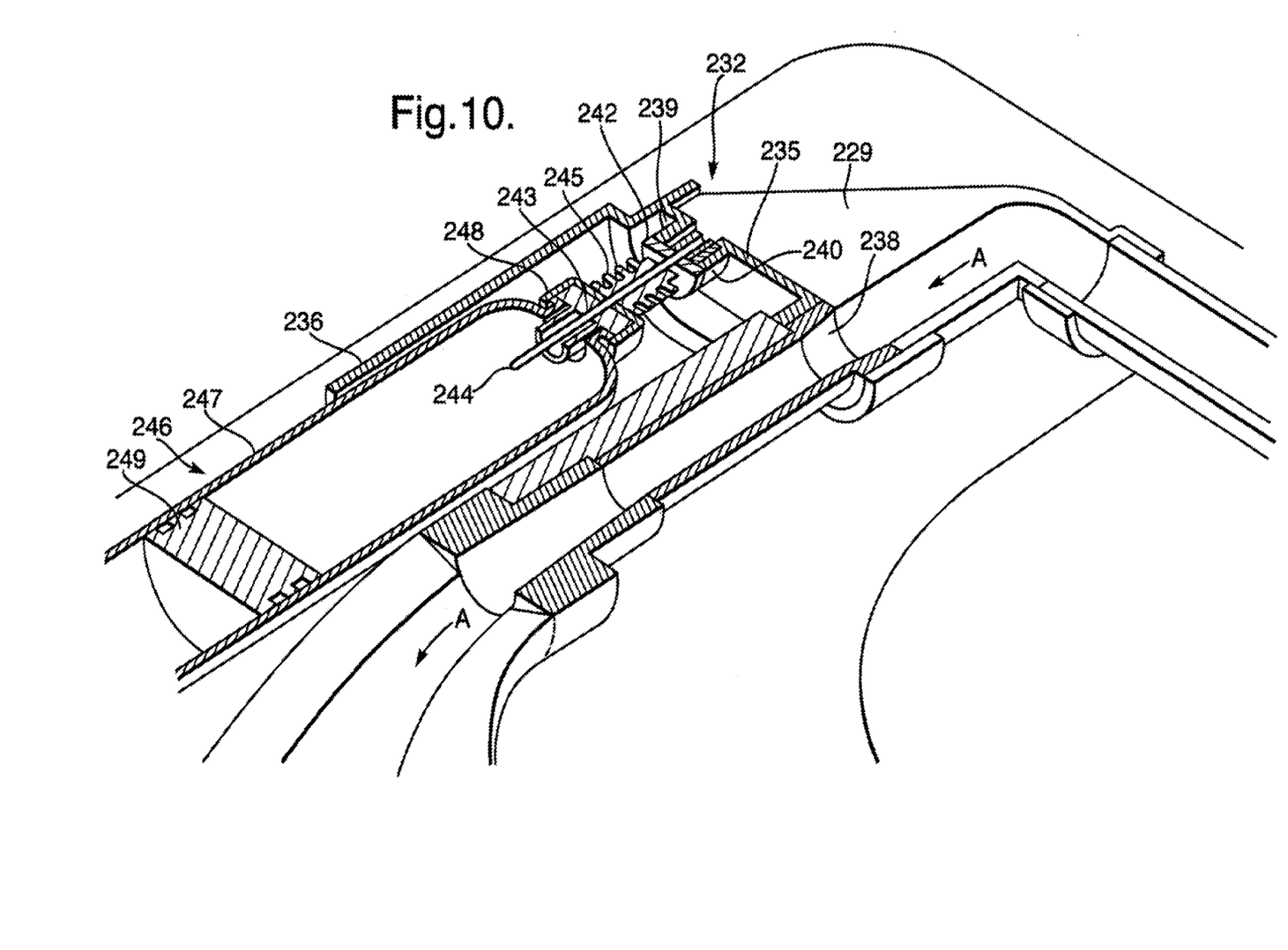
FIG. 10 is a cutaway view of part of the cassette of FIG. 7 showing the parts associated with introduction of liquid into the chamber.

The pump is then started by pressing the on/off switch 276. It quickly reaches a steady state in which the gas is circulating in the loop chamber steadily in the direction of arrow A in FIG. 10. At this point, the user applies pressure to the plunger shaft 250 to dispense polidocanol into the loop chamber 206. Referring to FIG. 10, the action of applying pressure to the plunger shaft 250 overcomes the resistance offered by the interference fit between the carpoule socket 236 and carpoule 246, causing the carpoule to move against the needle assembly 241. Up until this time, the atmosphere in the loop has been sealed from contact with the contents of the carpoule and from the internal atmosphere in the cassette housing by means of the sheath 245 covering the needle 243. As the carpoule septum cap 248 moves against the sheath 245, the sheath is moved back and the needle 243 pierces the sheath 245 and then the septum cap 248. In this way, communication is made between the contents of the carpoule and the contents of the loop, without any risk of significant lost sterility or nitrogen ingress.

After the connection is made, the user continues to apply pressure to the plunger shaft 250 which now causes the plunger head 249 to move down the vial 247, dispensing the polidocanol liquid through the needle 243 and into the channel 235 to the porous sinter ring 238. The liquid is evenly distributed around the cross section of the loop chamber 206 at that point and is introduced evenly into the flowing gas immediately before the gas and liquid pass through the foam generator 208. Liquid and gas continue to circulate and the foam is gradually refined until a steady state is reached after 30-60 seconds.

The foam can be maintained in this way for as long as desired, though this may have sterility implications which are addressed by a modified version of the device which deactivates after a given period of use (see below). The user may withdraw foam at any time by switching off the pump and fitting a conventional e.g. 20 ml syringe to the luer outlet 203 on the cassette. The outlet 203 is valved using a system well known in this field so that insertion of the syringe luer nozzle opens the valve and allows foam to be withdrawn. Since the luer port 203 and outlet tube 231 may provide dead spots where sub-standard foam may accumulate, the use withdraws a quantity of foam, e.g. 5 ml and in any event sufficient so that the foam entering the syringe can be seen to be of good quality, and then discards it before re-inserting the syringe and withdrawing foam for use. This procedure has the additional benefit that the dead space in the syringe nozzle is also purged of air. Once a syringe of foam has been withdrawn, the use switches the pump back on to maintain the remaining foam in the cassette in good condition in case more foam is required later in the procedure.

In a modification of this embodiment the pump is designed to shut down after 30 minutes of continuous operation in order to safeguard sterility. In the modified embodiment, an RFID (radio frequency identification) tag is incorporated into the cassette housing, and an RFID reader incorporated into the pump unit. In this way, each cassette is uniquely identifiable by the pump unit, which is programmed to deactivate 30 minutes after the cassette is fitted to the machine and only to re-activate when a new cassette is fitted.

The invention claimed is:

1. A foam generating device for generating therapeutic foam, comprising:
    a sealed chamber formed as an endless loop defining a continuous pathway containing foamable liquid or gas;
    a sealed container containing gas or foamable liquid; the sealed container being arranged for the selective introduction of its contents into the sealed chamber such that the sealed chamber then contains both gas and foamable liquid and has a predetermined initial volume;
    a foam generating structure located within the sealed chamber in the continuous pathway;
    whereby circulation of the gas and liquid around the continuous pathway through the foam generating structure within the chamber generates a therapeutic foam.

2. The foam generating device as claimed in claim 1 wherein the container is initially charged with liquid and the sealed chamber is initially charged with gas.

3. A foam generating device as claimed in claim 1 wherein the sealed container and the sealed chamber are located in a common housing.

4. The foam generating device as claimed in claim 3, wherein the said housing with the sealed chamber and the sealed container located therein forms a disposable cassette, unit or consumable.

5. The foam generating device as claimed in claim 1, wherein the sealed chamber is of variable volume such that, on introduction of gas or liquid from the sealed container, it is capable of increasing its volume by 10% to reach the predetermined initial volume, without substantial change in the pressure in the sealed chamber.

6. The foam generating device as claimed in claim 5, wherein, on extraction of therapeutic foam from the sealed chamber, the sealed chamber is further capable of reducing its volume by 20% or more from the predetermined initial volume, without substantial change in the pressure in the sealed chamber, whilst still permitting circulation of gas and liquid to maintain the remaining foam in the sealed chamber.

7. The foam generating device as claimed in claim 1 wherein the sealed chamber wall is at least partly of flexible or compressible material.

8. The foam generating device as claimed in claim 3 wherein the common housing is provided with an aperture through which a flexible or compressible part of the sealed chamber wall is configured for engagement by an external pump in order to circulate the contents of the sealed chamber.

9. The foam generating device as claimed in claim 1 further comprising a pump adapted to circulate the contents of the sealed chamber through the foam generating structure.

10. The foam generating device as claimed in claim 9 wherein the pump is external to the sealed chamber and is adapted to engage with a wall of the sealed chamber in order to circulate the contents of the sealed chamber through the foam generating structure.

11. The device as claimed in claim 3 wherein the common housing is adapted to be mounted on the pump such that, in use, the gas and liquid circulate within the sealed chamber in a substantially horizontal plane.

12. The foam generating device as claimed in claim 1 wherein the sealed chamber has an access means for a syringe luer nozzle or needle for withdrawing the therapeutic foam.

13. The foam generating device as claimed in claim 5, wherein the sealed chamber is capable of increasing its volume by 20% or more.

14. The foam generating device as claimed in claim 6, wherein the sealed chamber is capable of reducing its volume by 50% or more.

* * * * *